(12) United States Patent
Kumar et al.

(10) Patent No.: US 7,763,748 B2
(45) Date of Patent: Jul. 27, 2010

(54) PROCESS FOR PREPARATION OF HIGHLY PURE ISOTRETINOIN

(75) Inventors: Ashok Kumar, Maharashtra (IN); Dharmendra Singh, Maharashtra (IN); Ganesh Devidas Mahale, Maharashtra (IN); Ragnesh Kumar Rana, Maharashtra (IN); Mahesh Kharade, Maharashtra (IN)

(73) Assignee: IPCA Laboratories Limited, Mumbai (IN)

( * ) Notice: Subject to any disclaimer, the term of this patent is extended or adjusted under 35 U.S.C. 154(b) by 0 days.

(21) Appl. No.: 12/034,310

(22) Filed: Feb. 20, 2008

(65) Prior Publication Data

US 2008/0207946 A1    Aug. 28, 2008

(51) Int. Cl.
*A61K 31/203* (2006.01)
(52) U.S. Cl. .................................................. 562/510
(58) Field of Classification Search ........................ None
See application file for complete search history.

(56) References Cited

U.S. PATENT DOCUMENTS 6,441,226 B1 * 8/2002 Salman et al. ............... 562/510
6,740,337 B2 * 5/2004 Pant et al. ................... 424/451
2003/0042166 A1 * 3/2003 Waterman .................... 206/528
2005/0192351 A1 * 9/2005 Mossi et al. ................. 514/559

FOREIGN PATENT DOCUMENTS

GB    2035120    *  6/1980

OTHER PUBLICATIONS

Buchwald et al Advanced Synthetic Catalysis, 2006, 348, pp. 23-39.*

* cited by examiner

*Primary Examiner*—Daniel M Sullivan
*Assistant Examiner*—Yevegeny Valenrod
(74) *Attorney, Agent, or Firm*—Blank Rome LLP

(57) ABSTRACT

The present invention relates to a process for preparation of isotretinoin and more specifically, to a purification process for obtaining highly pure isotretinoin that is useful as a keratolytic agent, particularly useful for the treatment of acne. The process involves treating isotretinoin containing metal contamination and/or other impurities with a base in a suitable solvent to form a solution of isotretinoin, followed by adsorption, precipiation, and filtration or centrifugation.

19 Claims, No Drawings

PROCESS FOR PREPARATION OF HIGHLY PURE ISOTRETINOIN

FIELD OF THE INVENTION

The present invention relates to a process for preparation of isotretinoin and more specifically, to a purification process for obtaining highly pure isotretinoin that is useful as a keratolytic agent, particularly useful for the treatment of acne.

BACKGROUND OF THE INVENTION

Isotretinoin (Formula I), also known as 13-cis-retinoic acid, is a medication used for the treatment of severe acne. It is sometimes used in prevention of certain skin cancers. It is a retinoid, meaning it is derived from vitamin A and is found in small quantities naturally in the body. Oral isotretinoin is marketed under various trade names, most commonly Accutane. It inhibits the sebaceous gland function and keratinization and is used for the treatment of dermatological diseases. It is very effective in very severe and nodulosystic acne and prevents scarring.

As mentioned above, isotretinoin whose structure represented in Formula I, structurally is a highly conjugated molecule consisting of a substituted cyclohexene moiety and a nine carbon polyene side chain with a terminal free carboxyl group. All but the C-13 double bond in the side chain possess cis geometry and therefore known as 13-cis-retinoic acid.

Commercially available β-ionone has been conveniently used for the construction of the cyclohexene portion of isotretinoin. There are ample literatures available for the preparation of isotretinoin exploring various synthetic alternatives. For example by the process described in J. Organic Chemistry, 54, 2620-2628, 1989; J. Chem. Soc. (Comm), 1984-97, 1968; US Patent Application Publication No. 20050192351; and U.S. Pat. No. 4,556,518. Most commonly used process starts from [3-methyl-5(2,6,6-trimethyl-1-cyclohene-1yl-2,4-pentadienyl]-triphenyl-phosphonium)halide, which is condensed with 5-hydroxy-1methyl-2(5-H)-furanone. However, this condensation reaction yields a mixture of isomers of retinoic acid including the 11,13-di-cis-retinoic acid (Formula II), 9,13,-di-cis-retinoic acid (formula III), all-trans-retinoic acid (Formula IV) and 13-cis-retinoic acid (isotretinoin).

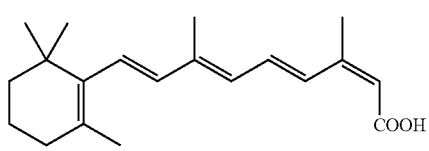

Isotretinoin
(Formula I)

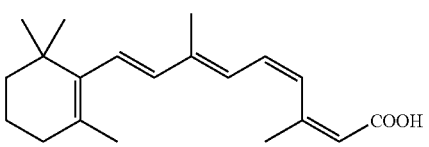

11,13-dicisretinoic acid
(Formula II)

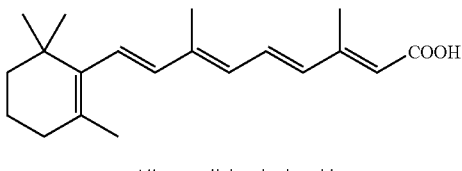

All-trans-dicisretinoic acid
(Formula IV)

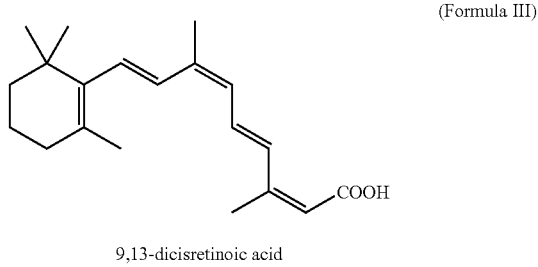

9,13-dicisretinoic acid
(Formula III)

To improve the yield of the 13-cis isomer, the above mixture is subjected to isomerization reaction where the undesired isomers are converted to the desired 13-cis-retinoic acid. The isomerization reaction is effected either by use of heavy metal catalysts such as rhodium or palladium (see US Patent Application Publication No. 20050192351 and U.S. Pat. No. 4,556,518) or by photochemical isomerization (see U.S. Pat. No. 6,177,579); however, in the photo-chemical isomerization reaction, the yield of 13-cis-retinoic acid is very low (nearly 44%). The metal catalyzed isomerization reaction provides a higher isomeric conversion in the order of greater than 97%; however, the product obtained is contaminated with the heavy metals (in the order of about 30000-40000 ppm after isolation), which does not meet the required purity for the drug, but also contribute to the known instability of the product (for the instability studies on isotretinoin, see Pharmaceutical Research, 1992, 9:1203-1208).

The crystallization methods so far reported do not effectively remove the trace metals, unless a thorough repeated crystallization from organic solvents is performed, which is not only unacceptable for stability of the compound but also for economy of the process. This is because, the solubility of isotretinoin in organic or aqueous solvents is very low; and as such, very high volume of solvents are required to completely dissolve the trace metal contaminated isotrentioin for crystallization. The higher temperature crystallization removes heavy metal to some extent, but such operations further degrades the product due to instability of isotretinoin under these conditions. Although isotretinoin is soluble in ethers or chlorinated hydrocarbons like methylene chloride, the crystallization from these solvents are not acceptable due to organic volatile impurities (OVI) issues and any further processing for removal of these solvents results in degradation of isotretinoin. Furthermore, it has been reported that the isomeric retinoic acids are rather unstable in organic solvents, which instability is partially due the presence of trace metals. Thus there is a long felt need in the art to get a process for effective removal of trace metals in isotretinoin, while providing stability to the isotretinoin. These objectives are accomplished by the present invention by providing an improved process for isotretinoin objectively for the removal of trace metals.

SUMMARY OF THE INVENTION

The present inventors had discovered that the prior art processes present substantial difficulties in producing pure isotretinoin substantially free of any trace metals in economically acceptable yield. The invention, therefore, aims to provide an improved process for making isotretinoin substantially free of trace metals. In accordance with one aspect, the invention provides a process for preparation of isotretinoin, which includes a base and acid mediated treatment of crude isotretinoin at suitable temperatures in suitable solvent. Aqueous solvents are found to be ideal for this application. The aqueous solvent is selected from water and water miscible solvents, such as primary, secondary, or tertiary alcohols, ketones, aprotic polar solvents (such as dimethylformamide, acetonitrile etc.). Preferably, the solvent for isolation is a mixture of water and an alcohol. Particularly preferred alcohol for this purpose is methanol, ethanol, and isopropanol.

In a preferred embodiment of the invention, the process is operated in presence of catalytic quantities of an antioxidant. The antioxidant may be, but is not limited to, appropriately butylated hydroxytoluene (BHT) or butylatedhydroxyanisole (BHA).

In a second aspect, the present invention provides an improved single-pot process for preparation of [3-methyl-5 (2,6,6-trimethyl-1-cyclohene-1-yl-2,4-pentadienyl]-triphenyl-phosphonium)halide, and its condensation with 5-hydroxy-1-methyl-2(5-H)-furanone for obtaining isotretinoin, which is further isomerized and purified according to the present invention.

DETAILED DESCRIPTION OF THE INVENTION

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows. Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

The term "isolating" is used to indicate separation or collection or recovery of the compound being isolated in the solid/liquid form either as crude or pure material.

The term "substantially free" in the context of trace metals means that the product is free from contamination of said trace metals not more than 20 ppm, preferably less than 10 ppm and most preferably less than 5 ppm. The term "substantially free" in the context of other chemical impurities means that the product is free from contamination of said impurities at less than 0.5%, preferably less than 0.1% and most preferably less than 0.05%.

The term "pure" as used herein means that the "pure" substance is substantially free of impurities, including trace metals and/or other isomers of the substance. As such, "pure" refers to at least 99.5% of the substance, preferably at least 99.8%, and most preferably at least 99.95%. Generally, the "pure" substance of the present application is isotretinoin.

It should be understood that there exists equilibrium between a free species and salt form of a compound capable of forming salt with bases/acids (e.g., by virtue of having a carboxylic acid functionality in the molecule).

The inventors of the present invention has found that the use of conventional solvent crystallization does not provide a reliable, consistent methodology to remove trace metals from isotretinoin. The inventors has recognized that small changes in manufacturing parameters might lead to impurities formation due to polymerization or oxidation of isotretinoin, thereby contaminating the product with those impurities. One such impurity is the oxidized products of isotretinoin whose content increases when subjected to crystallization conditions (e.g., prolong period of heating) due to photo-oxidation. The present inventors, on exploring various process alternatives, for a reliable process solution have found that the use of an improved purification procedure, which comprises treating the metal contaminated isotretinoin with a base in a suitable solvent to form a solution of isotretinoin, permits reliable and complete removal of trace metals from isotretinoin by adsorption followed by precipiation, and filtration or centrifugation. Aqueous solvents are ideal for this application. The isotretinoin from the aqueous solution can be isolated by treatment with an acid to obtain isotretinoin substantially free of trace metals and any oxidized impurities.

Although low temperature operation takes care of oxidative degradation, in one embodiment, it may be preferable to use catalytic quantity of an antioxidant to prevent any oxidation or formation of oxidized impurities. The antioxidants may be appropriately selected from butylated hydroxytoluene (BHT) or butylated hydroxyanisole (BHA).

Aqueous solvent used for the above treatment is preferably selected from water and water miscible solvents. Especially preferred water miscible organic polar solvents are alcohols; ketones, such as acetone; polar aprotic solvents, such as dimethyl formamide, acetonitrile, and dimethyl sulphoxide. Alcohols may be any straight chain or branched chain, especially methanol, ethanol and isopropanol. Especially preferred solvent is a combination of water and the above organic solvents. The invention permits the use of very small quantities/volume of solvent for dissolution and purification, for example as low as 2 volume to 20 volume relative to starting material to be dissolved (for example, for 1 kg of starting material, 2 L to 20 L can be used), which also reflects on the economy and environmental friendliness of the process. The preferred percentage of water in the aqueous solvent ranges from 30 to 99%, and most preferrably 50%. Preferably, the reaction is performed under controlled temperature usually below 50° C., especially between −15 to +35° C.

The base used for dissolution of isotretinoin may be selected appropriately from an inorganic or organic class of compounds. The most preferred bases are sodium carbonate or bicarbonate, potassium carbonate and bicarbonate, hydroxides, lithium hydroxide, triethyl amine, methyl amine, ethyl amine, aqueous ammonia etc. The acid used for recovery of isotretinoin from the aqueous basic solution is selected from an appropriate organic or inorganic acid. Hydrochloric acid is especially preferred for this application.

In a preferred process condition, the isotretinoin containing trace metals and possible other impurities (crude isotretinoin) is dissolved in a basic aqueous solution at a temperature ranging from −15 to 35° C. Preferably, it is dissolved at a temperature between 0-5° C. in about 5 volume (L) of aqueous solution relative to the crude isotretinoin (kg) (e.g. 5 L of aqueous solvent for each kg of crude isotretinoin). The aqueous base solution of isotretinoin is filtered to remove any undissolved materials and trace metals. This solution is then treated with an acid, especially inorganic acid, to precipitate the isotretinoin from the aqueous solution. The precipitated solid is isolated from the solvent by conventional means such as filtration or centrifugation.

The isotretinoin, obtained by any known methods and further isomerized with a metal catalyst such as rhodium or palladium, can be purified by the method of the present invention, which effectively removes chemical impurities and trace metals.

In a second aspect, the present invention provides a single-pot process for the preparation of [3-methyl-5(2,6,6-trimethyl-1-cyclohene-1yl-2,4-pentadienyl]-triphenyl-phosphonium) halide, and its condensation with 5-hydroxy-1-methyl-2(5-H)-furanone for obtaining isotretinoin as a mixture of isomers (see below scheme 1 where the halide is chloride).

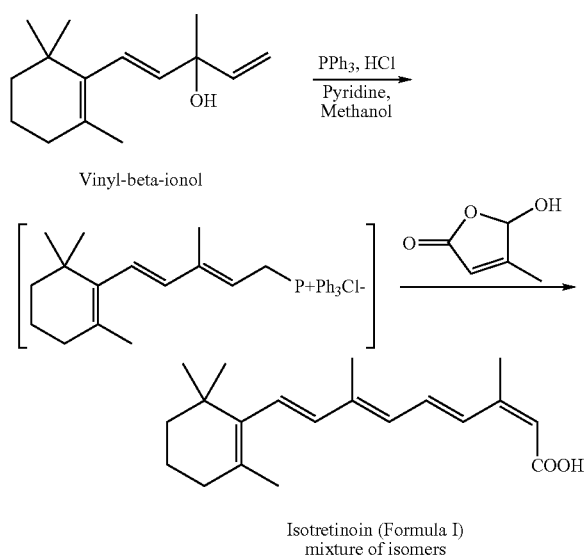

Scheme 1

Vinyl-beta-ionol

Isotretinoin (Formula I)
mixture of isomers

The process comprises treating the vinyl-β-ionol (Formula V) with triphenylphosphine (PPh₃) in presence of a acid salt at a pH in the range of 6.0 to 7 in a solvent to form [3-methyl-5(2,6,6-trimethyl-1-cyclohene-1yl-2,4-pentadienyl]-triphenyl-phosphonium) halide which is further treated with 5-hydroxy-1-methyl-2(5-H)-furanone in presence of a base. The acid salt is usually a mineral acid salt, preferably pyridinium hydrochloride. Although base can be appropriately selected from organic or inorganic bases, inorganic bases are preferred for this application. Especially preferred bases are potassium hydroxide, or sodium hydroxide. The solvents are selected from non-aqueous solvents, especially alcohols. Methanol, ethanol and isopropanol are especially preferred for this reaction. The molar ratio of the reactants and reagents may appropriately chosen, however, equi-molar amounts or slight excess of 5-hydroxy-1-methyl-2(5-H)-furanone relative to the starting [3-methyl-5(2,6,6-trimethyl-1-cyclohene-1-yl-2,4-pentadienyl]-triphenyl-phosphonium) halide is employed for economy of the process. The reaction can be effected at or below reflux temperature of the solvent used in the reaction, preferably below 50° C., and most preferably below 20° C.

The reaction yields a mixture of isomers of retinoic acid wherein the content of 13-cis-retinoic acid (isotretinoic acid) is about 20-25%. The isomeric mixture is then subjected to isomerization into 13-cis-retinoic acid using metal catalyst, for example, with palladium nitrate in an organic solvent. Polar aprotic solvents are preferred for this reaction as a reaction medium, especially ethyl acetate and acetonitrile. After isomerization the product shows the following isomer content:

| | |
|---|---|
| 13-cis-retinoic acid | 98.5% |
| 9,13-dicis-retinoic acid | 0.2 to 0.3% |
| 11,13-dicis-retinoic acid | 0.4 to 0.5% |
| all-trans-retinoic acid | 0.1 to 0.2% |
| palladium | 30000-40000 ppm |
| Oxidized impurities | 0.05 to 0.1% |

The palladium contaminated isotretinoin is purified according to the afore-described process of the present invention and the product of the following purity is obtained:

| | |
|---|---|
| 13-cis-retinoic acid | >99.5% |
| 9,13-dicis-retinoic acid | 0.05 to 0.1% |
| 11,13-dicis-retinoic acid | 0.05 to 0.1% |
| all-trans Retinoic acid | 0.02 to 0.1% |
| Oxidized impurity | 0.05 to 0.1% |
| palladium | 0-10 ppm |

The product after drying is also substantially free of bound organic solvents. Substantially free of organic solvents herein means that the bound solvents are not more than 5000 ppm, preferably not more than 1000 ppm and most preferably less than 100 ppm.

The process conditions are further illustrated in the Examples. It is surprising that the highly unstable isotretinoin is stable under the operative conditions of the present invention which permits reliable purification from heavy metals. The results of the invention are therefore unexpected.

Also provided in accordance with the invention are pharmaceutical compounds comprising isotretinoin in substantially pure form, free from the oxidized impurities and trace metals. Preferably, the isotretinoin present in such compositions is obtained in substantially pure form by means of the process of the invention before being incorporated into a pharmaceutical product.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

EXAMPLE 1

Retinoic Acid Isomers 100 grams of vinyl-β-ionol was taken in 1500 ml methanol at room temperature. To the dissolved solution of vinyl-β-ionol, pyridine (42 ml), hydrochloric acid (42 ml at 30%) and Triphenyl phosphine (116.8 g) were added. The solution was then heated to reflux and maintained for 1 hour. The reaction mass was cooled; and 5-hydroxy-1-methyl-2(5-H)-furanone (44.2 g) and potassium hydroxide (77 g) was added and stirred at −10 to 15° C. for 3 hours. After completion of the reaction, the solvent was distilled under vacuum to yield a residue containing a mixture of retinoic acid isomers (100 g).

EXAMPLE 2

Retinoic Acid Isomers 100 grams of vinyl-β-ionol was taken in 1500 ml methanol at room temperature. To the dissolved solution of vinyl-β-ionol, pyridine (42 ml), hydrochloric acid (42 ml of 30%), and triphenyl phosphine (116.8 g) were added. The solution was then heated to reflux and maintained for 1 hour. The methanol was removed in a vacuum; and isopropanol (1000 ml) was added into the reaction. The reaction solution was cooled to −10° C.; and 5-hydroxy-1-methyl-2(5-H)-furanone (44.2 gm) and potassium hydroxide (77.28 gm in 760 ml isopropanol) was added and stirred at −15 to −10° C. for 2.5 hours. The crude product was isolated by extraction with ethyl acetate and hexane mixture, followed by washing with aqueous methanol and evaporation of the organic solvent.

EXAMPLE 3

Isomerization 100 gm of isotretinoin isomers obtained as described in Example 1 or 2 was suspended in 150 ml ethyl acetate. The solution was heated to 50° C.; and the catalyst (prepared by mixing 100 mg palladium nitrate, 24 ml acetonitrile and 480 mg triethyl amine) was added into the solution. The mixture was maintained at 50° C. for 1 hour. The solution was then cooled to 30° C. and then chilled to below −5 degrees and maintained for 1.5 to 2 hours. The precipitated product was filtered, washed with chilled ethanol (100 ml), and dried to obtain the crude product weighing 60 g.

EXAMPLE 4

Purification of Isotretinoin from Isopropanol (IPA)/KOH

In a flask, 1000 ml isopropanol, 23 g potassium hydroxide and 0.1 g BHT were mixed well. The mixture was cooled to below −5° C.; and 100 g crude isotretinoin from Example 3 was added and stirred until dissolution. The solution was treated with activated charcoal and filtered; and 1000 ml water was added to the filtrate. The pH of the solution was adjusted with 1N HCl to pH 4-5. The precipitated product was filtered, washed with water followed by chilled ethanol, and dried to obtain 98 g of pure isotretinoin (99.7% and heavy metal content less than 5 ppm).

EXAMPLE 5

Purification from IPA/Aqueous Ammonia

In a flask, 1000 ml isopropanol and 27 ml liquor ammonia were mixed well. The mixture was cooled to below −5° C.; and 100 g crude isotretinoin from Example 3 was added and stirred until dissolution. The solution was treated with activated charcoal and filtered; and 1000 ml water was added to the filtrate. The pH of the solution was adjusted with 1N HCl to pH 4-5. The precipitated product was filtered, washed with water followed by chilled ethanol, and dried to obtain 98 g pure isotretinoin (99.7% and heavy metal content less than 5 ppm).

EXAMPLE 6

Purification Using Acetonitrile/Triethylamine

In a flask, 1000 ml acetonitrile and 80 ml triethylamine were mixed well. The mixture was cooled to below −5° C.; and 100 g crude isotretinoin from Example 3 and 0.1% butylated hydroxytoluene were added and stirred until dissolution. The solution was treated with activated charcoal and filtered; and 1000 ml water was added to the filtrate. The pH of the solution was adjusted with 1N HCl to pH 4-5. The precipitated product was filtered, washed with water followed by chilled ethanol, and dried to obtain 97 g pure isotretinoin (99.7% and heavy metal content not detected).

EXAMPLE 7

Purification Using Water/NaOH/Acetone

In a flask, 1000 ml water, 500 ml acetone, 16 g sodium hydroxide, and 0.1 g butylatedhydroxyanisole were mixed well. The mixture was cooled to below −5° C.; and 100 g crude isotretinoin from Example 3 was added and stirred until dissolution. The solution was treated with activated charcoal (10 g), filtered; and 1000 ml water was added to the filtrate. The pH of the solution was adjusted with hydrochloric acid to pH 4-5. The precipitated product was filtered, washed with water followed by chilled ethanol, and dried to obtain 97 g pure isotretinoin (99.7% purity and heavy metal content less than 5 ppm).

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A process for purifying isotretinoin contaminated with heavy metal and/or other impurities comprising the steps of:
   a. dissolving the heavy metal and/or other impurities contaminated isotretinoin with a base in a solvent to obtain a solution comprising an isotretinoin salt;
   b. adding an adsorbent to the solution; and
   c. recovering isotretinoin substantially free from heavy metal and/or other impurities.

2. The process as claimed in claim 1, wherein said base is an organic or inorganic base.

3. The process as claimed in claim 1, wherein the base is a metal hydroxide.

4. The process as claimed in claim 1, wherein the base is ammonia or mono, di, or trialkyl amine.

5. The process as claimed in claim 1, wherein the solvent is polar protic or aprotic solvent.

6. The process as claimed in claim 1, wherein the solvent is selected from water, alcohols, ketones, amides, nitriles or dimethylsulphoxide or their combinations thereof.

7. The process as claimed in claim 1, wherein the solvent is selected from acetone, methanol, ethanol, isopropanol, water, acetonitrile, dimethylformamide, or mixtures thereof.

8. The process as claimed in claim 1, wherein the purification is carried out in presence of an antioxidant.

9. The process as claimed in claim 8, wherein the antioxidant is butylated hydroxytoluene or butylated hydroxyanisole.

10. The process as claimed in claim 1, wherein the process operates at a temperature below about 50° C.

11. The process as claimed in claim 10, wherein the temperature ranges from about −15 to +35° C.

12. The process as claimed in claim 1, wherein the recovering step comprising treatment of isotretinoin solution of step b with an acid.

13. The process as claimed in claim 12, wherein the acid is an organic or inorganic acid.

14. The process as claimed in claim 12, wherein the acid is hydrochloric acid.

15. The process as claimed in claim 2, wherein the recovering step comprising treatment of isotretinoin solution with an acid.

16. The process as claimed in claim 1, wherein the crude isotretinoin is prepared by a single pot process comprising
   i. reacting vinyl-β-ionol with triphenylphosphine in presence of hydrochloric acid and pyridine to form a reaction mass comprising [3-methyl-5(2,6,6-trimethy-1-cyclohene-1yl-2,4-pentadienyl]-triphenyl-phosphonium) chloride;
   ii. treating said reaction mass with 5-hydroxy-1-methyl-2 (5-H)-furanone in presence of a base to yield a mixture of retinoic acid isomers; and
   iii. transforming said mixture of retinoic acid isomers into 13-cis retinoic acid (isotretinoin).

17. The process as claimed in claim 16, wherein the said base in step ii is metal hydroxide such as potassium hydroxide.

18. The process as claimed in claim 16, wherein the step iii is carried out in presence of a metal catalyst such as palladium.

19. The process as claimed in claim 1, wherein the isotretinoin is produced by:
   a. reacting vinyl-β-ionol with triphenylphosphine in presence of hydrochloric acid and pyridine to form a reaction mass comprising [3-methyl-5(2,6,6-trimethy-1-cyclohene-1yl-2,4-pentadieny]-triphenyl-phosphonium) chloride;
   b. treating said reaction mass with 5-hydroxy-1-methyl-2 (5-H)-furanone in presence of a base to yield a mixture of isomeric retinoic acid; and
   c. transforming said isomeric retinoic acid into 13-cis retinoic acid (isotretinoin).

* * * * *